(12) United States Patent
Pease

US012220449B2

(10) Patent No.: US 12,220,449 B2
(45) Date of Patent: Feb. 11, 2025

(54) ENHANCING T CELL ACTIVATION USING ALTERED MHC-PEPTIDE LIGANDS

(71) Applicant: Mayo Foundation for Medical Education and Research, Rochester, MN (US)

(72) Inventor: Larry R. Pease, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1128 days.

(21) Appl. No.: 17/009,613

(22) Filed: Sep. 1, 2020

(65) Prior Publication Data

US 2020/0397877 A1   Dec. 24, 2020

Related U.S. Application Data

(60) Division of application No. 15/135,832, filed on Apr. 22, 2016, now Pat. No. 10,792,348, which is a continuation of application No. 13/299,754, filed on Nov. 18, 2011, now abandoned.

(60) Provisional application No. 61/415,227, filed on Nov. 18, 2010.

(51) Int. Cl.

| | |
|---|---|
| *C12N 7/00* | (2006.01) |
| *A61K 35/17* | (2015.01) |
| *A61K 39/00* | (2006.01) |
| *C07K 14/74* | (2006.01) |
| *G01N 33/50* | (2006.01) |
| *G01N 33/569* | (2006.01) |
| *A61K 38/00* | (2006.01) |

(52) U.S. Cl.
CPC .......... *A61K 39/0011* (2013.01); *A61K 35/17* (2013.01); *A61K 39/0008* (2013.01); *A61K 39/001106* (2018.08); *A61K 39/00115* (2018.08); *A61K 39/001151* (2018.08); *A61K 39/001153* (2018.08); *A61K 39/001156* (2018.08); *A61K 39/001157* (2018.08); *A61K 39/001162* (2018.08); *A61K 39/00117* (2018.08); *A61K 39/001182* (2018.08); *A61K 39/001186* (2018.08); *A61K 39/001188* (2018.08); *A61K 39/001191* (2018.08); *A61K 39/001192* (2018.08); *A61K 39/001193* (2018.08); *A61K 39/001194* (2018.08); *A61K 39/001197* (2018.08); *A61K 39/4611* (2023.05); *A61K 39/4621* (2023.05); *A61K 39/46433* (2023.05); *C07K 14/70539* (2013.01); *C12N 7/00* (2013.01); *G01N 33/505* (2013.01); *G01N 33/56977* (2013.01); *A61K 38/00* (2013.01); *A61K 2039/53* (2013.01); *A61K 2039/572* (2013.01); *C12N 2710/10043* (2013.01); *G01N 2333/70539* (2013.01)

(58) Field of Classification Search
None
See application file for complete search history.

(56) References Cited

U.S. PATENT DOCUMENTS

| | | |
|---|---|---|
| 5,580,859 A | 12/1996 | Stoves et al. |
| 5,589,466 A | 12/1996 | Felgner et al. |
| 2012/0141537 A1 | 6/2012 | Pease |
| 2016/0361402 A1 | 12/2016 | Pease |

FOREIGN PATENT DOCUMENTS

WO   WO 2010/037395   4/2010

OTHER PUBLICATIONS

HLA Nomenclature (2023, 2 pages) (Year: 2023).*
Singh et al (J. Immunol. 2017, 199:2203-2213) (Year: 2017).*
Liu et al (Immunogenetics, 2006, 58: 339-346) (Year: 2006).*
Breckpot et al (Gene Ther., 2007,14: 847-862) (Year: 2007).*
Fissolo et al (Molec. Cellular Proteomics, 2009, 8: 2090-2101) (Year: 2009).*
Attay et al., "Ham-2 corrects the class I antigen-processing defect in RMA-s cells," Nature, 1992, 355(6361):647-649.
Berman et al., "The Protein Data Bank," Acta Crystallogr D Biol Crystallogr., 58(Pt 6 No 1):899-907, Epub May 29, 2002.
Berzofsky et al., "Approaches to improve engineered vaccines for human immunodeficiency virus and other viruses that cause chronic infections," Immunol. Rev., 1999, 170:151-172.
Blanas et al., "Induction of Autoimmune Diabetes by Oral Administration of Autoantigen," Science, 1996, 274:1707-1709.
Daniels et al., "Thymic selection threshold defined by compartmentalization of Ras/MAPK signaling," Nature., 444(7120):724-729, Epub Nov. 1, 2006.
De Felipe et al., "Targeting of proteins derived from self-processing polyproteins containing multiple signal sequences," Traffic, 5(8):616-626, Aug. 2004.
Degano et al., "A functional hot spot for antigen recognition in a superagonist TCR/MHC complex," Immunity, 12(3):251-261, Mar. 2000.
Ding et al., "Four A6-TCR/peptide/HLA-A2 structures that generate very different T cell signals are nearly identical," Immunity, 11(1):45-56, Jul. 1999.
Dyall et al., "Heteroclitic immunization induces tumor immunity," J Exp Med., 188(9):1553-1561, Nov. 2, 1998.
England et al., "Molecular analysis of a heteroclitic T cell response to the immunodominant epitope of sperm whale myoglobin. Implications for peptide partial agonists," J. Immunol., 1995, 155(9):4295-4306.
Fahey and Schooley, "Status of immune-based therapies in HIV infection and AIDS," Clin Exp Immunol., 88(1):1-5, Apr. 1992.

(Continued)

*Primary Examiner* — Michael Szperka
*Assistant Examiner* — Marianne Dibrino
(74) *Attorney, Agent, or Firm* — Fish & Richardson P.C.

(57) ABSTRACT

Materials and methods for identifying and using MHC molecule variants for activating self-reactive T cells in a peptide-specific manner, and their use to focus autoimmune cellular responses against diseases such as cancers and persisting viral infections, are described.

2 Claims, 6 Drawing Sheets

Figure 1C:
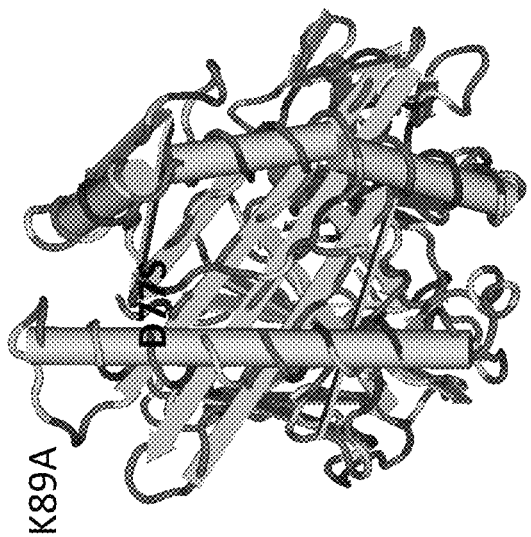

Specification includes a Sequence Listing.

(56) References Cited

OTHER PUBLICATIONS

Feng et al. "Structural evidence for a germline-encoded T cell receptor-major histocompatibility complex interaction 'codon'," Nat. Immunol., 2007, 8(9):975-983.
Finn, "Cancer vaccine: between the idea and the reality," Nat. Rev. Immunol., 2003, 3:630-641.
Fournier and Schirrmacher, "Randomized clinical studies of antitumor vaccination: state of the art in 2008," Expert Rev Vaccines., 8(1):51-66, Jan. 2009.
Gagnon et al., "T cell receptor recognition via cooperative conformational plasticity," J Mol Biol., 363(1):228-243, Epub Aug. 22, 2006.
Garboczi et al., "Structure of the complex between human T-cell receptor, viral peptide and HLA-A2," Nature, 384: 134-141, 1996.
Garcia et al. "αβ T Cell receptor interactions with syngeneic and allogeneic ligands: Affinity measurements and crystallization," Proc. Nat. Acad. Sci. USA, 1997, 94:13838-13843.
Garcia et al., "Structural basis of plasticity in T cell receptor recognition of a self peptide-MHC antigen," Science, 279(5354):1166-1172, Feb. 20, 1998.
Garcia et al., "Structural basis of T cell recognition," Annu. Rev. Immunol., 1999, 17:369-397.
Gil et al., "T cell receptor engagement by peptide-MHC ligands induces a conformational change in the CD3 complex of thymocytes," J Exp Med., 201(4):517-522, Feb. 21, 2005.
Godfrey et al., "The fidelity, occasional promiscuity, and versatility of T cell receptor recognition," Immunity, 28(3):304-314, Mar. 2008.
Greaves et al., "Clonal evolution in cancer," Nature, 481(7381):306-313, Jan. 18, 2012.
Haile et al., "Tumor cell programmed death ligand 1-mediated T cell suppression is overcome by coexpression of CD80," J Immunol., 186(12):6822-6829, Epub May 9, 2011.
Hemmi et al., "Three spontaneous H-2Db mutants are generated by genetic micro-recombination (gene conversion) events. Impact on the H-2-restricted immune responsiveness," J. Exp. Med., 1988, 168(6):2319-2335.
HLA Nomenclature (2015) (Year: 2015).
Hoffmann et al., "The ability of variant peptides to reverse the nonresponsiveness of T lymphocytes to the wild-type sequence p53(264-272) epitope," J Immunol., 168(3):1338-1347, Feb. 1, 2002.
Horton et al., "Characterization of the spontaneous mutant H-2Kbm29 indicates that gene conversion in H-2 occurs at a higher frequency than detected by skin grafting," J Immunol., 147(9):3180-3184, Nov. 1, 1991.
Hunt et al., "Structural basis of Kbm8 alloreactivity. Amino acid substitutions on the beta-pleated floor of the antigen recognition site," J. Immunol., 1990, 145:1456-1462.
Hyrup and Nielsen, "Peptide Nucleic Acids (PNA): Synthesis, properties and potential applications," Bioorgan. Med. Chem., 1996, 4:5-23.
Jenkins et al., "On the composition of the preimmune repertoire of T cells specific for Peptide-major histocompatibility complex ligands," Annu Rev. Immunol., 2010, 28:275-294.
Jones et al., "Distinct CDR3 conformations in TCRs determine the level of cross-reactivity for diverse antigens, but not the docking orientation," The Journal of Immunology, 181(9):6255-6264, Nov. 1, 2008.
King et al., "T cell affinity regulates asymmetric division, effector cell differentiation, and tissue pathology," Immunity, 37(4):709-720, Oct. 19, 2012.
Klebanoff et al., "Therapeutic cancer vaccines: are we there yet?" Immunol Rev., 239(1):27-44, Jan. 2011.
Kuhns et al., "T cell receptor interactions with class I heavy-chain influence T cell selection," Proc Natl Acad Sci U S A., 97(2):756-760, Jan. 18, 2000.
Kurts et al., "CD8 T cell ignorance or tolerance to islet antigens depends on antigen dose," Proc Natl Acad Sci U S A., 96(22):12703-12707, Oct. 26, 1999.
Leach et al., "Enhancement of antitumor immunity by CTLA-4 blockade," Science, 271(5256):1734-1736, Mar. 22, 1996.
Lehuen et al., "Immune cell crosstalk in type 1 diabetes," Nat. Rev. Immunol., 2010, 10:501-513.
Letvin, "Progress in the development of an HIV-1 vaccine," Science, 280(5371):1875-1880, Jun. 19, 1998.
Llano et al., "An essential role for LEDGF/p75 in HIV integration," Science, 314(5798):461-464, Epub Sep. 7, 2006.
Luz et al., "Structural comparison of allogeneic and syngeneic T cell receptor-peptide-major histocompatibility complex complexes: a buried alloreactive mutation subtly alters peptide presentation substantially increasing V(beta) Interactions," J Exp Med., 195(9):1175-1186, May 6, 2002.
Machuca et al., "Human immunodeficiency virus type 2 infection in Spain. The HIV-2 Spanish Study Group," Intervirology, 42(1):37-42, 1999.
Maile et al., "Peripheral "CD8 tuning" dynamically modulates the size and responsiveness of an antigen-specific T cell pool in vivo," J. Immunol., 2005, 174(2):619-627.
Mareeva et al., "How a T cell receptor-like antibody recognizes major histocompatibility complex-bound peptide," J Biol Chem., 283(43):29053-29059, Epub Aug. 14, 2008.
Marrack et al., "Evolutionarily conserved amino acids that control TCR-MHC interaction," Annu. Rev. Immunol., Apr. 2008, 26:171-203.
Mumberg et al., "Unique tumor antigens redefined as mutant tumor-specific antigens," Semin Immunol., 8(5):289-293, Oct. 1996.
Nava-Parada et al., "Peptide vaccine given with a Toll-like receptor agonist is effective for the treatment and prevention of spontaneous breast tumors," Cancer Res., 67(3):1326-1334, Feb. 1, 2007.
Nicholson et al., "T cell recognition of self and altered self antigens," Crit Rev Immunol., 17(5-6):449-462, 1997.
Nikolich-Žugich et al., "The many important facets of T-cell repertoire diversity," Nature Reviews Immunology, Feb. 2004, 4(2):123-32.
Parham et al., "Nature of polymorphism in HLA-A, -B, and -C molecules," Proc. Natl. Acad. Sci. U.S.A., 85(11):4005-9, Jun. 1988.
Parks et al., "Breaking tolerance with engineered class I antigen-presenting molecules," PNAS, 116(8):3136-3145 (2019).
Pavelko et al., "Theiler's murine encephalomyelitis virus as a vaccine candidate for immunotherapy," PLoS One, 6(5):e20217, Epub May 20, 2011.
Pease et al., "Spontaneous H-2 mutants provide evidence that a copy mechanism analogous to gene conversion generates polymorphism in the major histocompatibility complex," Proc Natl Acad Sci U S A., 80(1):242-246, Jan. 1983.
Pulido et al., "Using virally expressed melanoma cDNA libraries to identify tumor-associated antigens that cure melanoma," Nat Biotechnol., 30(4):337-343, Mar. 18, 2012.
Pullen et al., "Recognition of a single amino acid change on the surface of a major transplantation antigen is in the context of self peptide," J Immunol., 152(7):3445-3452, Apr. 1, 1994.
Pullen et al., "The functional significance of two amino acid polymorphisms in the antigen-presenting domain of class I MHC molecules. Molecular dissection of Kbm3," J Immunol., 143(5):1674-1679, Sep. 1, 1989.
Rannnnensee et al., "MHC Ligands and Peptide Motifs," Landes Bioscience, Springer, NY, Austin, pp. 33-49, 1997.
Sakuma et al., "Lentiviral vectors: basic to translational," Biochem J., 443(3):603-618, May 1, 2012.
Schreiber et al., "Tumor immunogenicity and responsiveness to cancer vaccine therapy: the state of the art," Semin Immunol., 22(3):105-112, Epub Mar. 11, 2010.
Schultze et al., "B7-mediated costimulation and the immune response," Blood Rev., 10(2):111-127, Jun. 1996.
Schumacher and Schreiber, "Neoantigens in cancer immunotherapy," Science, Apr. 2015, 348(6230):69-74.
Setlur et al., "Tumor archaeology reveals that mutations love company," Cell, 149(5):959-961, May 25, 2012.

(56) References Cited

OTHER PUBLICATIONS

Sha et al., "Positive selection of transgenic receptor-bearing thymocytes by Kb antigen is altered by Kb mutations that involve peptide binding," Proc Natl Acad Sci U S A., 87(16):6186-6190, Aug. 1990.

Singh et al., "Emerging concepts in TCR specificity: rationalizing and (maybe) predicting outcomes," The Journal of Immunology, Oct. 2017, 199(7):2203-13.

Sloan-Lancaster et al., "Altered peptide ligand-induced partial T cell activation: molecular mechanisms and role in T cell biology," Annu Rev Immunol., 14:1-27, 1996.

Stratton, "Exploring the genomes of cancer cells: progress and promise," Science, 331(6024):1553-1558, Mar. 25, 2011.

Suarez et al., "Synergistic effects of CTLA-4 blockade with tremelimumab and elimination of regulatory T lymphocytes in vitro and in vivo," Int J Cancer, 129(2):374-386, Epub Nov. 16, 2010.

Summerton and Weller, "Morpholino Antisense Oligomers: Design, Preparation, and Properties," Antisense Nucleic Acid Drug Dev., 1997, 7:187-195.

Szymczak-Workman et al., "Generation of 2A-linked multicistronic cassettes by recombinant PCR," Cold Spring Harb Protoc., 2012(2):251-254, Feb. 1, 2012.

Tallquist et al., "A single T cell receptor recognizes structurally distinct MHC/peptide complexes with high specificity," J Exp Med., 184(3):1017-1026, Sep. 1996.

Tallquist et al., "Alloreactive 2C T cells recognize a self peptide in the context of the mutant Kbm3 molecule," J Immunol., 155(5):2419-2426, Sep. 1995.

Tallquist et al., "Degenerate recognition of alloantigenic peptides on a positive-selecting class I molecule," J Immunol., 160(2):802-809, Jan. 15, 1998.

Thompson et al., "Tumor masses support naive T cell infiltration, activation, and differentiation into effectors," J Exp Med., 207(8):1791-1804, Epub Jul. 26, 2010.

UniprotKB-Q95381 (uniprot.org/uniprot/Q95381, Feb. 1997), Feb. 1997, 5 pages.

Walunas et al., "CTLA-4 can function as a negative regulator of T cell activation," Immunity, 1: 405-413, 1994.

Woolhouse et al., "Human viruses: discovery and emergence," Philosophical Transactions of the Royal Society B: Biological Sciences, Oct. 2012, 367(1604):2864-71.

\* cited by examiner

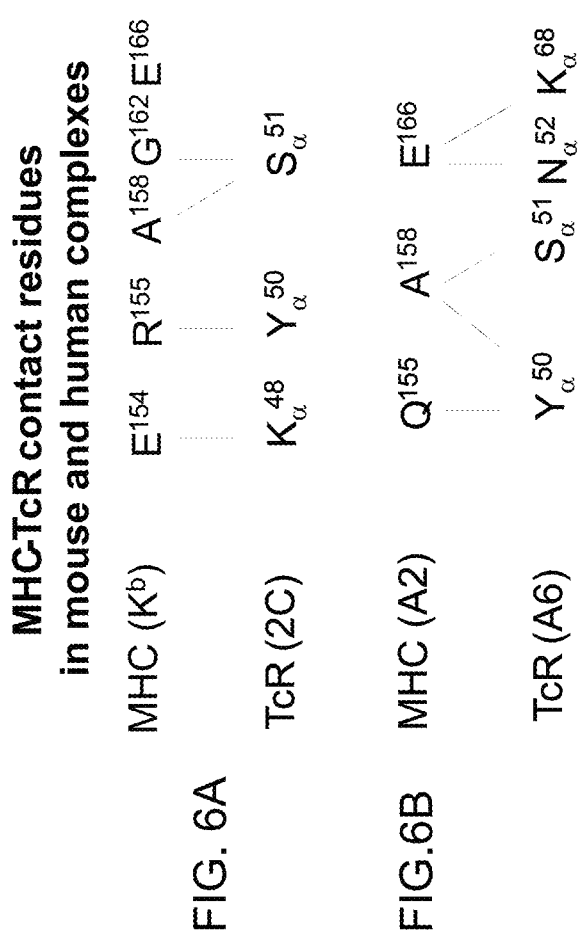

```
SEQUENCE LISTING

<160> NUMBER OF SEQ ID NOS: 5

<210> SEQ ID NO 1
<211> LENGTH: 8
<212> TYPE: PRT
<213> ORGANISM: Artificial Sequence
<220> FEATURE:
<223> OTHER INFORMATION: synthetic peptide

<400> SEQUENCE: 1

Ser Ile Ile Asn Phe Glu Lys Leu
1               5

<210> SEQ ID NO 2
<211> LENGTH: 8
<212> TYPE: PRT
<213> ORGANISM: Artificial Sequence
<220> FEATURE:
<223> OTHER INFORMATION: synthetic peptide

<400> SEQUENCE: 2

Ser Ile Ile Asn Phe Glu Gln Leu
1               5

<210> SEQ ID NO 3
<211> LENGTH: 8
<212> TYPE: PRT
<213> ORGANISM: Artificial Sequence
<220> FEATURE:
<223> OTHER INFORMATION: synthetic peptide

<400> SEQUENCE: 3

Glu Ile Ile Asn Phe Glu Lys Leu
1               5

<210> SEQ ID NO 4
<211> LENGTH: 8
<212> TYPE: PRT
<213> ORGANISM: Artificial Sequence
<220> FEATURE:
<223> OTHER INFORMATION: synthetic peptide

<400> SEQUENCE: 4

Ser Ile Ile Gly Phe Glu Lys Leu
1               5

<210> SEQ ID NO 5
```

-continued

```
<211> LENGTH: 8
<212> TYPE: PRT
<213> ORGANISM: Artificial Sequence
<220> FEATURE:
<223> OTHER INFORMATION: synthetic peptide

<400> SEQUENCE: 5

Ser Ile Ile Gln Phe Glu His Leu
1               5
```

ENHANCING T CELL ACTIVATION USING ALTERED MHC-PEPTIDE LIGANDS

CROSS-REFERENCE TO RELATED APPLICATIONS

This application is a divisional of U.S. application Ser. No. 15/135,832, filed Apr. 22, 2016, which is a continuation of U.S. application Ser. No. 13/299,754, filed Nov. 18, 2011 (Abandoned), which claims benefit of priority from U.S. Provisional Application Ser. No. 61/415,227, filed on Nov. 18, 2010.

STATEMENT AS TO FEDERALLY SPONSORED RESEARCH

This invention was made with government support under AI028320 awarded by the National Institutes of Health. The federal government has certain rights in the invention.

SEQUENCE LISTING

This application contains a Sequence Listing that has been submitted electronically as an ASCII text file named "SEQ.txt." The ASCII text file, created on Sep. 1, 2020, is 1264 bytes in size. The material in the ASCII text file is hereby incorporated by reference in its entirety.

TECHNICAL FIELD

This document relates to materials and methods for activating self-reactive T cells in a peptide-specific manner, to focus autoimmune T cellular responses against, for example, cancers and persisting virus infections.

BACKGROUND

During development of the repertoire of the normal T cell population, affinity/avidity thresholds for cellular activation are set, defined by the ability of the expressed T cell receptors to bind to major histocompatibility complex (MHC) molecules that present peptide epitopes derived from the body's own proteins (Jenkins et al. (2010) *Annu. Rev. Immunol.* 28:275-294). This means that T cells bearing antigen-specific T cell receptors (TCR) capable of binding self peptides presented by self MHC molecules are not present functionally in the immune repertoire. T cells with receptors just below this affinity/avidity threshold are presumably present, but they are believed to be functionally blind to self antigen.

A T cell response can be visualized as having two phases with respect to cellular activation. The first is the transition of naïve T cells to activated T cells. This happens when T cells first encounter non-self antigens presented by MHC molecules capable of binding their receptors with affinity/avidity above the set activation threshold. Once these cells are activated, they undergo a series of cell divisions, acquire a primed state characterized by the development of effector function capabilities, and enter the blood in search of cells expressing the inciting antigen presented in the context of self MHC. Upon engaging the inciting antigen presented in the context of self MHC in the peripheral tissues, the primed T cells release cytokines and granule proteins, inducing cell death and controlling the replication and infectivity of pathogens. The threshold for reactivation of primed cells is thought to be lower than the threshold for generating primed cells from naïve cells.

SUMMARY

The normal immune system contains T cells (e.g., CD4$^+$ and CD8$^+$ T cells) bearing antigen-specific TCR that are composed of two chains (mostly α and β chains), and that are not normally reactive to self. This document is related in part to the development of methods to prime self-reactive T cells in a peptide specific manner, and the discovery that the primed self-reactive T cells can execute their effector functions in peripheral tissues with specificity. Thus, activated cells of this kind can be incorporated into therapeutic schemes to focus autoimmune cellular responses against, for example, cancers and persisting pathogenic (e.g., viral) infections.

In one aspect, this document features a method for treating a subject in need thereof. The method can include administering to the subject (a) a cell expressing on its surface a variant of a MHC molecule, the variant having one or more amino acid changes from wild-type in the part of the MHC molecule that interacts with a T cell receptor, where the cell has been identified as having the ability to activate a T cell in the presence of an epitope from the subject, and (b) the epitope or a polypeptide comprising the epitope, wherein the subject has a pathological condition that is amenable to therapy by a T cell immune response. The subject can be a human. At least one of the one or more amino acid changes can be at a residue of the MHC molecule that, on the surface of a cell expressing the MHC molecule, is accessible for interaction with a TCR. The MHC molecule can be an HLA-A0201 MHC class I molecule, where at least one of the one or more amino acid changes is at position 72, 76, 79, 154, 158, 162, or 166 of the molecule. The epitope can be from a polypeptide associated with the pathological condition. For example, the pathological condition can be cancer and the epitope can be from a polypeptide expressed by a cancer cell, or the pathological condition can be caused by an infectious microorganism and the epitope can be from a polypeptide expressed by a cell infected with the infectious microorganism. In some embodiments, the epitope can be from a survivin, GP100, MelA, survivin-2B, livin/ML-IAP, Bcl-2, Mcl-1, Bcl-X(L), mucin-1, NY-ESO-1, telomerase, CEA, MART-1, HER-2/neu, bcr-abl, PSA, PSCA, tyrosinase, p53, hTRT, leukocyte proteinase-3, hTRT, gpl OO, MAGE antigens, GASC, JMJD2C, JARD2 (JMJ), JHDM3a, WT-1, CA 9, or protein kinase polypeptide.

In another aspect, this document features a composition that includes (a) a cell expressing on its surface a variant of an MHC molecule, the variant having one or more amino acid changes from wild-type in the part of the MHC molecule that interacts with a T cell receptor, wherein the cell has been identified as having the ability to activate a T cell in the presence of a particular peptide epitope; and (b) a pharmaceutically acceptable carrier; and optionally, the peptide epitope. At least one of the one or more amino acid changes can be at a residue of the MHC molecule that is accessible for interaction with a TCR. The MHC molecule can be an HLA-A0201 MHC class I molecule, wherein at least one of the one or more amino acid changes is at position 72, 76, 79, 154, 158, 162, or 166 of the molecule. The peptide epitope can be from a polypeptide expressed by a cancer cell or by a cell infected with an infectious microorganism. For example, the peptide epitope can be from a survivin, GP100, MelA, survivin-2B, livin/ML-IAP, Bcl-2, Mcl-1, Bcl-X(L), mucin-1, NY-ESO-1, telomerase, CEA, MART-1, HER-2/neu, bcr-abl, PSA, PSCA, tyrosinase, p53, hTRT, leukocyte proteinase-3, hTRT, gpl OO, MAGE antigens, GASC, JMJD2C, JARD2 (JMJ), JHDM3a, WT-1, CA 9, or protein kinase polypeptide. The pharmaceutically acceptable carrier can be selected from the group consisting of water, saline solution, binding agents, fillers, lubricants, disintegrates, and wetting agents. The composition can further comprise an adjuvant selected from the group consisting of Freund's adjuvant, aluminum hydroxide, lysolecithin, pluronic polyols, polyanions, peptides, oil emulsions, keyhole limpet hemocyanin, dinitrophenol, cytokines, and bacterial products.

In another aspect, this document features a method that includes contacting a cell in a subject with a virus particle containing a nucleic acid that encodes a variant of an MHC molecule, the variant having one or more amino acid changes from wild-type in a portion of the MHC molecule that interacts with a T cell receptor. The subject can be a human. The virus can be an adenovirus. The MHC molecule can be a class I MHC molecule.

In yet another aspect, this document features a variant of an MHC molecule, where the variant has one or more amino acid changes from wild-type in the part of the MHC molecule that interacts with a T cell receptor, and where the MHC molecule, in the presence of a particular peptide epitope, has been identified as having the ability to activate a T cell.

This document also features a method of selecting a MHC molecule variant for activation of an immune response. The method can include: providing a panel of cells, each cell of the panel expressing on its surface a variant of an MHC molecule, the variant having one or more amino acid changes from wild-type in the part of the MHC molecule that interacts with a T cell receptor; testing the ability of each cell of the panel to activate a T cell in the presence of a selected peptide epitope; and selecting the MHC molecule expressed by a cell of the panel that activates a T cell in the presence of the peptide epitope.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a depiction of the structure of a TCR:MHC: Peptide complex (2C TcR:H-2Kb:pdEV8; Garcia et al. (1997) Proc. Nat. Acad. Sci. USA 94:13838-13843; and Garcia et al. (1998) *Science* 279:1166-1172) derived from x-ray crystallographic data. FIG. 1B is a depiction of the structure of an Ab (antibody):MHC:Peptide complex (25-D1.16:H-2Kb:pdEV8; Mareeva et al. (2008) J. Biol. Chem. 283:29053-29059) derived from x-ray crystallographic data. FIG. 1C is a depiction of the structure of an MHC heavy chain (derived from x-ray crystallographic data), showing the Kbm3 mutations (D77S and K89A).

FIG. 2 is a graph plotting percent lysis in an OT-1 T cell killing assay. OT-1 T cells activated with the Kb-SIINFEKL (SEQ ID NO: 1) pMHC-peptide complex lysed EL4 (Kb) targets presenting SIINFEKL (SEQ ID NO:1), while OT-1 T cells activated with the Kb-Q7 (SEQ ID NO:2) pMHC-peptide complex did not. OT1 spleen cells were cultured with 10 μg/ml peptide in culture for 5 days prior to use in a standard $^{51}$Cr release cytotoxicity assay against target cells (EL4 or EL4 pulsed with the SIINFEKL (SEQ ID NO:1) peptide or the Q7 (SEQ ID NO:2) peptide.

FIG. 3 is a graph plotting percent lysis in an OT-1 T cell killing assay. OT-1 cells activated with the Kb-SIINFEKL (SEQ ID NO:1) pMHC-peptide complex lysed EL4 (Kb) target cells presenting SIINFEKL (SEQ ID NO:1) or Q7 (SEQ ID NO:2) peptide, but not EL4 cells not pulsed with peptide. OT-1 T cells were activated and assayed as in FIG. 2.

FIG. 4 is a graph plotting lack of diabetes occurrence in RIP-OVA mice challenged with OT-1 and Q7 peptide (SEQ ID NO:2) pulsed antigen presenting cells (APCs).

FIG. 5 is a graph plotting growth of lymphoma tumor grafts in wild type (B6) mice or in mice having an amino acid substitution in the peptide binding domain of the H-2 K (bm3 and bm8) or D (bm14) class I antigen presenting molecules. The lymphoma cells grew out in the wild type B6 hosts genetically matched with the tumor, but were rejected in the mutant mice.

FIGS. 6A and 6B are diagrams showing comparable molecular interactions defined for mouse 2C TcR CDR2α region with H-2Kb α2 helix (FIG. 6A) (Garcia (1998), supra) and for human A6 TcR CDR2α with the HLA-A0201 α2 of heavy chain (FIG. 6B) (Garboczi et al. (1996) *Nature* 384:134-141).

DETAILED DESCRIPTION

This document provides materials and methods for priming self-reactive T cells in a peptide specific manner, such that the cells can execute their effector functions in peripheral tissues (cancers and pathogen infected cells) with specificity. Activated cells of this kind can be incorporated into therapeutic schemes to focus autoimmune cellular responses against cancers and persisting virus infections, for example.

MHC genes contain polymorphisms, and vary greatly from individual to individual. There are two general classes of MHC molecules. Class I MHC (pMHC) molecules are found on almost all cells and present peptides to cytotoxic T lymphocytes (CTL). Class II MHC molecules are found mainly on antigen-presenting immune cells (APCs), which ingest polypeptide antigens (in, for example, microbes) and digest them into peptide fragments. The MHC-II molecules then present the peptide fragments to helper T cells, which, after activation, provide generally required helper activity for responses of other cells of the immune system (e.g., CTL or antibody-producing B cells).

The interaction between the peptide bound in the binding cleft of the heavy chain of MHC class I (pMHC) and the complementary determining regions (CDR) of the T cell receptor (TCR) determines the potential for T cell activation during the afferent and efferent stages of cellular immunity. The affinity that exists between TCR and MHC-peptide complex regulates T cell fate during development, initial activation, and during execution of effector functions. The crystal structure of the TCR/MHC complex indicates that the highly variable CDR3 regions of the Vα and Vβ domains determine the energetics of TCR/MHC interactions, with the predominate contacts occurring between the TCR CDR3 regions and peptide bound by the MHC molecule.

This document provides isolated MHC polypeptides that contain one or more (e.g., one, two, three, four, five, more than five, or any range between one and five) substitutions, additions, or deletions. As used herein, a "polypeptide" is any chain of amino acid residues, regardless of post-translational modification (e.g., phosphorylation or glycosylation). An "isolated" polypeptide is a polypeptide that (1) is not associated with proteins found in nature, (2) is free of other proteins from the same source (e.g., free of human proteins), (3) is expressed by a cell from a different species, or (4) does not occur in nature. An isolated polypeptide can be, for example, encoded by DNA or RNA, including synthetic DNA or RNA, or some combination thereof.

The polypeptides provided herein can contain an amino acid tag. A "tag" is generally a short amino acid sequence that provides a ready means of detection or purification through interactions with an antibody against the tag or through other compounds or molecules that recognize the tag. For example, tags such as c-myc, hemagglutinin, polyhistidine, or FLAG® can be used to aid purification and detection of a polypeptide. As an example, a polypeptide with a polyhistidine tag can be purified based on the affinity of histidine residues for nickel ions (e.g., on a Ni-NTA column), and can be detected in western blots by an antibody against polyhistidine (e.g., the Penta-His antibody; Qiagen, Valencia, CA). Tags can be inserted anywhere within the polypeptide sequence, although insertion at the amino- or carboxy-terminus is particularly useful.

The quality of the TCR/MHC interaction can be changed in both positive and negative directions by altering the peptides at their interface with the CDR3 loops of the TCR. The data presented herein show that changes in the structure of the MHC heavy chain can increase pMHC binding to the TCR, enhancing T cell activation. Rosetta Protein Modeling Suite, a computer modeling approach, was used to design more efficient pMHC to stimulate T cells in a peptide-dependent manner. The naturally occurring mouse pMHC molecule H-2Kbm3 mutant was of particular interest, due to a single point mutation existing at position 77 of the heavy chain that increases TCR/pMHC affinity.

This document also provides methods for generating a library of modified MHC (e.g., pMHC) molecules, and methods for using the library in selection of a particular modified MHC that can potentiate an immune response against a particular peptide. For example, an MHC heavy chain can be modified to contain one or more (e.g., one, two, three, four, five, or more than five) amino acid substitutions, deletions, or additions. These modifications can be located, for example, at amino acid residues that are involved in interactions with TCR. In some cases, one or more modifications can be made to the two α-helices (between which lies the peptide binding cleft) of MHC molecules. Such amino acid residues would generally be on the "upper" surface of these α-helices that, on the surface of a cell expressing the MHC molecule, faces outwards from the cell and thus is most accessible for interaction with a TCR of a T cell in the vicinity of the cell expressing the MHC molecule. The modifications can be such that the affinity/avidity of the MHC-peptide complex for the TCR is altered (e.g., increased or decreased, compared to a wild type MHC heavy chain). Exemplary modifications to the mouse pMHC heavy chain are described in the Examples herein. These changes can be extrapolated to human MHC molecules.

In some embodiments, a modified MHC molecule can contain one or more conservative substitutions. Amino acid substitutions can be made, in some cases, by selecting substitutions that do not differ significantly in their effect on maintaining (a) the structure of the peptide backbone in the area of the substitution, (b) the charge or hydrophobicity of the molecule at the target site, or (c) the bulk of the side chain. For example, naturally occurring residues can be divided into groups based on side-chain properties: (1) hydrophobic amino acids (norleucine, methionine, alanine, valine, leucine, and isoleucine); (2) neutral hydrophilic amino acids (cysteine, serine, and threonine); (3) acidic amino acids (aspartic acid and glutamic acid); (4) basic amino acids (asparagine, glutamine, histidine, lysine, and arginine); (5) amino acids that influence chain orientation (glycine and proline); and (6) aromatic amino acids (tryptophan, tyrosine, and phenylalanine). Substitutions made within these groups can be considered conservative substitutions. Examples of useful substitutions include, without limitation, substitution of valine for alanine, lysine for arginine, glutamine for asparagine, glutamic acid for aspartic acid, serine for cysteine, asparagine for glutamine, aspartic acid for glutamic acid, proline for glycine, arginine for histidine, leucine for isoleucine, isoleucine for leucine, arginine for lysine, leucine for methionine, leucine for phenylalanine, glycine for proline, threonine for serine, serine for threonine, tyrosine for tryptophan, phenylalanine for tyrosine, and/or leucine for valine.

In some embodiments, a modified MHC chain (e.g., a pMHC heavy chain) can include one or more non-conservative substitutions. Non-conservative substitutions typically entail exchanging a member of one of the classes described above for a member of another class.

Methods for making modified polypeptides are known in the art. By way of example and not limitation, a polypeptide can be obtained by extraction from a natural source (e.g., from isolated cells, tissues or bodily fluids), by chemical synthesis (e.g., by solid-phase synthesis or other methods well known in the art, including synthesis with an ABI peptide synthesizer; Applied Biosystems, Foster City, CA), or by expression of a recombinant nucleic acid encoding the polypeptide. Thus, in addition to modified MHC polypeptides, this document provides isolated nucleic acids encoding modified MHC polypeptides as described herein. The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. An isolated nucleic acid can be, e.g., a recombinant DNA molecule of any length, provided one of the nucleic acid sequences normally found immediately flanking that recombinant DNA molecule in a naturally-occurring genome is removed or absent. Thus, an isolated nucleic acid can be, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acids can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence. A nucleic acid existing among hundreds to millions of other nucleic acids within, for example, cDNA libraries or genomic libraries, or gel slices containing a genomic DNA restriction digest, is not to be considered an isolated nucleic acid.

As used herein, the term "nucleic acid" refers to both RNA and DNA, including mRNA, cDNA, genomic DNA, synthetic (e.g., chemically synthesized) DNA, and nucleic acid analogs. The nucleic acid can be double-stranded or single-stranded, and where single-stranded, can be the sense strand or the antisense strand. In addition, nucleic acid can be circular or linear. Nucleic acid analogs can be modified at the base moiety, sugar moiety, or phosphate backbone to improve, for example, stability, hybridization, or solubility of a nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered, morpholino ring, or peptide nucleic acids, in which the deoxyphosphate backbone is replaced by a pseudopeptide backbone and the four bases are retained. See, for example, Summerton and Weller (1997) *Antisense Nucleic Acid Drug Dev.* 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoroamidite, or an alkyl phosphotriester backbone.

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase can be used to extend the oligonucleotides, resulting in a single, double-stranded nucleic acid molecule per oligonucleotide pair, which then can be ligated into a vector.

Isolated nucleic acids also can be obtained by mutagenesis. For example, a nucleic acid sequence encoding a MHC heavy chain polypeptide can be mutated using standard techniques such as, for example, oligonucleotide-directed mutagenesis and/or site-directed mutagenesis through PCR. See, *Short Protocols in Molecular Biology*, Chapter 8, Green Publishing Associates and John Wiley & Sons, Edited by Ausubel et al., 1992.

This document also provides vectors containing a nucleic acid provided herein. As used herein, a "vector" is a replicon, such as a plasmid, phage, or cosmid, into which another DNA segment can be inserted so as to bring about the replication of the inserted segment. A vector can be an expression vector. An "expression vector" is a vector that includes one or more expression control sequences, and an "expression control sequence" is a DNA sequence that controls and regulates the transcription and/or translation of another DNA sequence.

In an expression vector provided herein, the nucleic acid can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A coding sequence is "operably linked" and "under the control" of expression control sequences in a cell when RNA polymerase is able to transcribe the coding sequence into mRNA, which then can be translated into the polypeptide encoded by the coding sequence.

Suitable expression vectors include, without limitation, plasmids and viral vectors derived from, for example, bacteriophage, baculoviruses, tobacco mosaic virus, herpes viruses, cytomegalovirus, retroviruses, poxviruses, adenoviruses, and adeno-associated viruses. Numerous vectors and expression systems are commercially available from such corporations as Novagen (Madison, WI), Clontech Laboratories (Mountain View, CA), Stratagene (La Jolla, CA), and Invitrogen/Life Technologies (Carlsbad, CA).

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, CT) sequences typically are expressed as a fusion with the encoded polypeptide. Such tags can be inserted anywhere within the polypeptide including at either the carboxyl or amino terminus.

This document also provides host cells containing a nucleic acid molecule and/or nucleic acid vector provided herein. The term "host cell" refers to prokaryotic cells and eukaryotic cells into which a nucleic acid molecule or vector can be introduced. Any method can be used to introduce nucleic acid into a cell. For example, naked DNA can be delivered directly to cells in vivo as described elsewhere (U.S. Pat. Nos. 5,580,859 and 5,589,466). In addition, calcium phosphate precipitation, electroporation, heat shock, lipofection, microinjection, and viral-mediated nucleic acid transfer can be used introduce nucleic acid into cells. In some cases, for example, a nucleic acid molecule (e.g., a cDNA) encoding a modified MHC molecule, a particular peptide epitope, or a polypeptide that includes a particular peptide epitope can be incorporated into a viral vector (e.g., an adenoviral vector, an adeno-associated virus vector, a herpes virus vector, a cytomegalovirus vector, a retrovirus vector, or a poxvirus vector). High titer virus can be prepared using standard methods, and the virus can be used to infect host cells such as, without limitation, cell lines in culture, or tumor cells in situ.

As described herein, a library or panel containing cells (e.g., RMAS cells) expressing modified MHC molecules can be generated. The cells in such a panel can be used in a screening method to determine which, if any, member or members of the panel contain a modified MHC molecule that can stimulate an immune response to a particular peptide. For example, a method can include providing a panel of cells, each of which expresses on its surface a variant of an MHC molecule, where the variant has one or more amino acid changes from wild-type in the part of the MHC molecule that interacts with a T cell receptor; testing the ability of each panel member to activate a T cell in the presence of a peptide epitope of interest; and selecting the MHC molecule expressed by a member of the panel that activates a T cell in the presence of the peptide epitope. Self peptides in general can be from proteins against which tolerance was established, but against which it is desired to activate a response because they are highly expressed in, for example, certain cancers. Thus, for example, a self peptide antigen from a cancer cell can be used as a peptide of interest, and a modified MHC molecule that stimulates an immune response against the peptide can be selected for potential therapeutic use. Examples of self peptides include, without limitation, peptides that are contained within proteins such as survivin, GP100, MelA, survivin-2B, livin/ML-IAP, Bcl-2, Mcl-1, Bcl-X(L), mucin-1, NY-ESO-1, telomerase, CEA, MART-1, HER-2/neu, bcr-abl, PSA, PSCA, tyrosinase, p53, hTRT, leukocyte proteinase-3, hTRT, gpl OO, MAGE antigens, GASC, JMJD2C, JARD2 (JMJ), JHDM3a, WT-1, CA 9, and protein kinases. See, also, WO 2010/037395, which discloses suitable cancer antigenic peptides.

In the methods provided herein, the modified MHC molecule can be a Class I (pMHC) or Class II molecule. Testing can be conducted in vivo or in vitro. In vitro testing can include, for example, the use of T cells from a cloned T cell line, a polyclonal T cell population, or T cells expressing recombinant TCR chains. The T cells can be CD4$^+$ or CD8$^+$ T cells. In vivo methods can include, e.g., administering to a subject (e.g., a human or a non-human mammal) one or more modified MHC molecules, nucleic acids encoding the one or more modified MHC molecule, or cells expressing the one or more modified MHC molecule, and testing for activation of T cell by the variant MHC-peptide complex by methods known in the art. A non-human mammal can be, e.g., a transgenic non-human mammal expressing a recombinant TCR (e.g., a human TCR) on, for example, all of its T cells, all of its CD4$^+$ T cells, or all of its CD8$^+$ T cells.

In some embodiments, an epitope of interest can be from any polypeptide against which an immune response is desired. For example, an epitope can be from a polypeptide expressed by a cancer cell, or by a cell infected with an infectious microorganism (e.g., a virus, bacteria, or protozoan). It is noted that an epitope (also referred to herein as a peptide epitope) "from" a particular polypeptide does not need to be physically isolated from that polypeptide, but also can be chemically synthesized or made recombinantly, for example, provided that the epitope has a sequence contained within the polypeptide.

This document also provides methods for treating an individual in need thereof (e.g., an individual in whom it is desired to stimulate an immune response against a particular peptide). The methods can include administering to the subject (a) a cell expressing on its surface a variant of an MHC molecule, where the variant has one or more amino acid changes from wild-type in the part of the MHC molecule that interacts with a T cell receptor, and where the cell has been identified as having the ability to activate a T cell (e.g., a CD4$^+$ T cell or a CD8$^+$ T cell) in the presence of a peptide epitope from the subject; and (b) the peptide epitope or a polypeptide containing the peptide epitope. The subject can have, or be likely to have, a pathological condition (e.g., cancer or an infectious disease, such as a viral, bacterial, or protozoan infection) that is amenable to therapy by a T cell immune response. A subject that is likely to have a pathological condition would be one having one or more symptoms of the condition. Symptoms of cancer and infectious diseases are well known in the art. The peptide epitope can be from a polypeptide that is expressed by a cancer cell or a cell infected with an infectious microorganism (e.g., a virus or an intracellular bacteria or protozoans).

The methods provided herein can include administering to a mammal (e.g., a human or a non-human mammal) an effective amount of a modified MHC polypeptide, nucleic acid encoding the modified MHC polypeptide, or cell expressing the modified MHC polypeptide or an effective amount of a composition containing such a polypeptide/nucleic acid/cell. In some cases, a method can include administering a nucleic acid encoding a modified MHC polypeptide by a virus-mediated transfer method (e.g., by direct injection into a selected tissue of viral particles encoding the modified MHC molecule).

As used herein, the term "effective amount" is an amount of a molecule, cell, or composition that is sufficient to increase an immune response against a peptide of interest. For example, in some embodiments, an "effective amount" of a cell expressing a modified MHC polypeptide can be an amount that is sufficient to increase T cell activation in a peptide specific manner. The degree of T cell activation can be determined by, for example, detecting or measuring CTL activity or helper activity [e.g., the production of cytokines such as interleukins (IL) (e.g., IL-2, IL-4, IL-5, IL-10, IL-12, or IL-13), or interferons (IFN) (e.g., IFN-α, IFN-β, or IFN-γ)]. Activation also can be assessed by flow cytometry (e.g., to look for particular antigen-specific cells, and to monitor populations of cells, such as CD4$^+$ vs. CD8$^+$ cells, or to look for CD2, CD27, CD28, CD45RA, CD45RO, CD62L, and/or CCR7, which are surface markers unique to T cells in various differentiation states). In some embodiments, T cell activation can be evaluated using ELISPOT, by adding the antigenic peptide optionally associated with a MHC monomer or MHC multimer or adding antigenic polypeptide comprising antigenic peptide, followed by measurement of IFN-gamma secretion from a population of cells or from individual cells. T cell activation also can be measured with quantaferon-like detection assays, e.g., using indirect detection, such as by adding the antigenic peptide optionally associated with a MHC monomer or MHC multimer or adding antigenic polypeptide comprising antigenic peptide, followed by measurement of IFN-gamma secretion from a population of cells or from individual cells.

In addition, this document provides compositions and methods for their administration to a subject. For example, the modified MHC polypeptides described herein, nucleic acids encoding the modified MHC polypeptides, or cells expressing the modified MHC polypeptides can be incorporated into compositions for administration to a subject (e.g., a subject having cancer or a viral or bacterial infection). In some embodiments, a composition can contain a peptide epitope of interest, or a polypeptide containing the peptide epitope.

Methods for formulating and subsequently administering therapeutic compositions are well known to those in the art. Dosages typically are dependent on the responsiveness of the subject to the composition, with the course of treatment lasting from a single treatment to several days or several months, or until a suitable response is achieved. Persons of ordinary skill in the art routinely determine optimum dosages, dosing methodologies and repetition rates. Optimum dosages can vary depending on the relative potency of a composition, and in some embodiments can be estimated based on the EC$_{50}$ found to be effective in in vitro and/or in vivo animal models.

This document also provides for the use of the peptides, polypeptides, nucleic acids, and cells disclosed herein in the manufacture of medicaments (e.g., for activating self-reactive T cells in a subject in a peptide-specific manner). The peptides, polypeptides, nucleic acids, or cells can be admixed, encapsulated, conjugated or otherwise associated with other molecules, molecular structures, or mixtures of compounds, such as liposomes, receptor or cell targeted molecules, or oral, topical or other formulations for assisting in uptake, distribution and/or absorption. In some embodiments, a composition can contain a peptide, polypeptide, nucleic acid, or cell as provided herein in combination with a pharmaceutically acceptable carrier and/or an adjuvant. Pharmaceutically acceptable carriers include, for example, pharmaceutically acceptable solvents, suspending agents, or any other pharmacologically inert vehicles for delivering polypeptides, nucleic acids, or cells to a subject. Pharmaceutically acceptable carriers can be selected with the planned manner of administration in mind so as to provide for the desired bulk, consistency, and other pertinent transport and chemical properties, when combined with one or more therapeutic compounds and any other components of a given pharmaceutical composition. Exemplary pharmaceutically acceptable carriers include, without limitation: water; saline solution; binding agents (e.g., polyvinylpyrrolidone or hydroxypropyl methylcellulose); fillers (e.g., lactose or dextrose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate). Exemplary adjuvants (e.g., that can be used to increase an immunological response) depend on the host species, and include, without limitation, Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Suitable adjuvants also include, for example, cytokines (e.g., interleukin-2 (IL-2), granulocyte-macrophage colony-stimulating factor (GM-CSF), IL-12, and IL-4) and bacterial products (e.g., lipopolysaccharides (LPS) and CpG). See, also, Finn (2003) *Nat. Rev. Immunol.* 3:630-641.

Pharmaceutical compositions containing molecules described herein can be administered by a number of methods. Administration can be, for example, parenteral (e.g., by subcutaneous, intrathecal, intraventricular, intramuscular, or intraperitoneal injection, or by intravenous (i.v.) drip); oral; topical (e.g., transdermal, sublingual, ophthalmic, or intranasal); or pulmonary (e.g., by inhalation or insufflation of powders or aerosols), or can occur by a combination of such methods. Administration can be rapid (e.g., by injection) or can occur over a period of time (e.g., by slow infusion or administration of slow release formulations).

This document also provides an article of manufacture that can include one or more modified MHC polypeptides as provided herein, nucleic acids encoding modified MHC polypeptides, and/or cells expressing modified MHC polypeptides (e.g., RMAS cells, or any other suitable type of cells). The article of manufacture can include the one or more polypeptides, nucleic acids, and/or cells formulated in a composition as described herein. In some embodiments, an article of manufacture also can contain one or more peptide epitopes to which modified MHC polypeptides can bind.

An article of manufacture can include, for example, a composition containing (a) a cell expressing on its surface a variant of an MHC molecule having one or more amino acid changes from wild-type in the portion of the MHC molecule that interacts with a T cell receptor, wherein the cell has been identified as having the ability to activate a T cell in the presence of a particular peptide epitope; and (b) a pharmaceutically acceptable carrier. Optionally, the article of manufacture can further include the peptide epitope. In some cases, the article of manufacture also can include an adjuvant as described herein (e.g., one or more cytokines, such as IL-2, IL-4, IL-5, IL-10, IL-12, IL-13, IFN-α, IFN-β, or IFN-γ).

The invention will be further described in the following examples, which do not limit the scope of the invention described in the claims.

EXAMPLES

Example 1—Enhancing T Cell Activation Using Altered MHC-Peptide Ligands

Altered peptide ligands for T cell receptors: There are two widely accepted schemes for priming T cells expressing low affinity receptors for self. First, the quantity of self-peptide presented by MHC can be increased to enhance the avidity of the receptor ligand interaction between T cells and antigen presenting cells (England et al. (1995) *J. Immunol.* 155:4295-4306; and Berzofsky et al. (1999) *Immunol. Rev.* 170:151-172). The second is to alter the structure of the peptide subtly to enhance the affinity of the MHC-peptide ligand for the T cell receptor (Maile et al. (2005) *J. Immunol.* 174 (2): 619-627). Both of these approaches require engineering each individual peptide antigen of interest, either to increase binding to MHC molecules or binding of the MHC-peptide complex to the T cell receptor. The methods described herein provide the option for increasing affinity of the MHC-peptide ligand for the T cell receptor for essentially all peptides, yet still maintaining peptide specificity in the antigen recognition process.

Figure 1B:
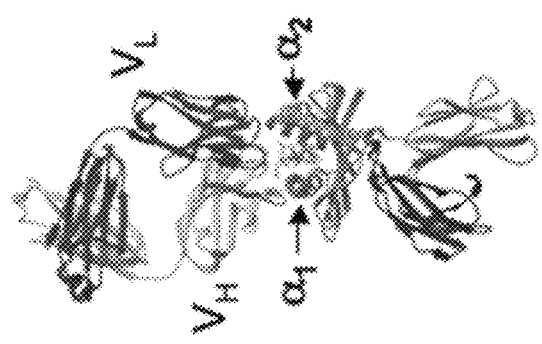
Figure 1A:
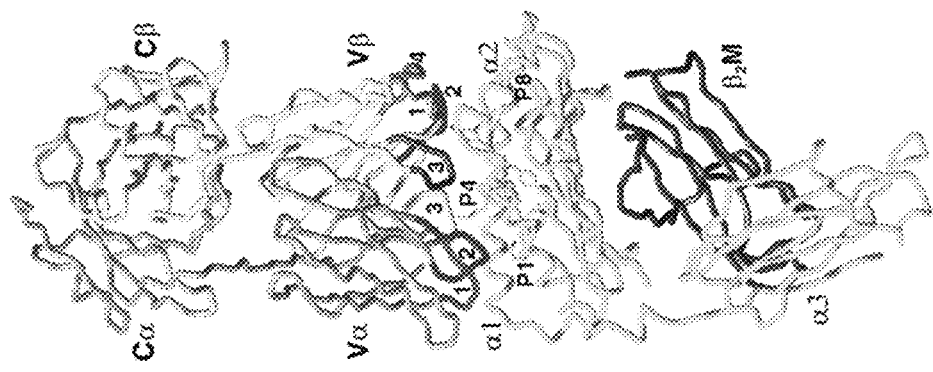

The three dimensional structure of the TCR interacting with MHC-peptide ligand (FIG. 1A) reveals a common mode of interaction. The complementarity determining regions (CDR, comprised of loops connecting beta strands of the immunoglobulin fold) of the TCR variable alpha (Vα) and beta (Vβ) chains interact with a surface comprised of the amino terminal alpha helical regions of the MHC proteins and the bound peptide (Garcia et al. (1998), supra; and Garcia et al. (1999) *Annu. Rev. Immunol.* 17:369-397). Key to the approach for generating altered MHC-peptide ligands as described herein are the observations derived from these early structural studies that the T cell receptor contact with the bound peptide is largely determined by the CDR3 segments and that the CDR1 and CDR2 segments of the T cell receptor interact mostly with the alpha helices of the MHC peptide presenting molecule. It was hypothesized that changes in the MHC molecule that primarily alter the interactions between the alpha helices and the T cell receptor in a way that generates a higher affinity interaction might enhance the T cell response to peptide antigens during the priming stage. Once these T cells achieve the primed state, they can be activated by the native MHC molecule presenting the same peptide. By generating a panel of altered MHC molecules that bind to the T cell receptor outside the CDR3 regions, a set of reagents that can be coupled with many different peptides can be assembled, without need for further engineering of the peptide antigens. Having a panel of "on the shelf" altered MHC ligands provides a practical alternative to the formidable task of engineering sets of peptides for antigen specific responses for each target of interest. This also provides a significant advance in the development of vaccines designed to break tolerance to weak cancer antigens, and might also be used to mobilize T cells remaining after the establishment of a persistent infection.

To demonstrate this principle, the following experiments were conducted, taking advantage of available reagents. The mouse OT-1 T cell expresses a defined T cell receptor that binds to the mouse H-2K$^b$ MHC molecule when complexed with a specific chicken ovalbumin peptide, SIINFEKL (SEQ ID NO:1). This T cell receptor MHC-peptide ligand interaction is sufficient to activate both the priming and effector stages of the T cell response. The antibody known as 25-D1.16 also binds to H-2K$^b$ specifically when the MHC molecule is complexed to the SIINFEKL (SEQ ID NO: 1) peptide. The degree that the 25-D1.16 antibody mimics T cell receptor binding is evident in the resolved three dimensional structure of the antibody:MHC:peptide complex (FIG. 1B), which demonstrates interactions of the antibody CDR regions and the MHC-peptide ligand resembling those of reported T cell receptor MHC-peptide three dimensional structures (Mareeva et al. (2008) *J. Biol. Chem.* 283:29053-29059).

Figure 2:
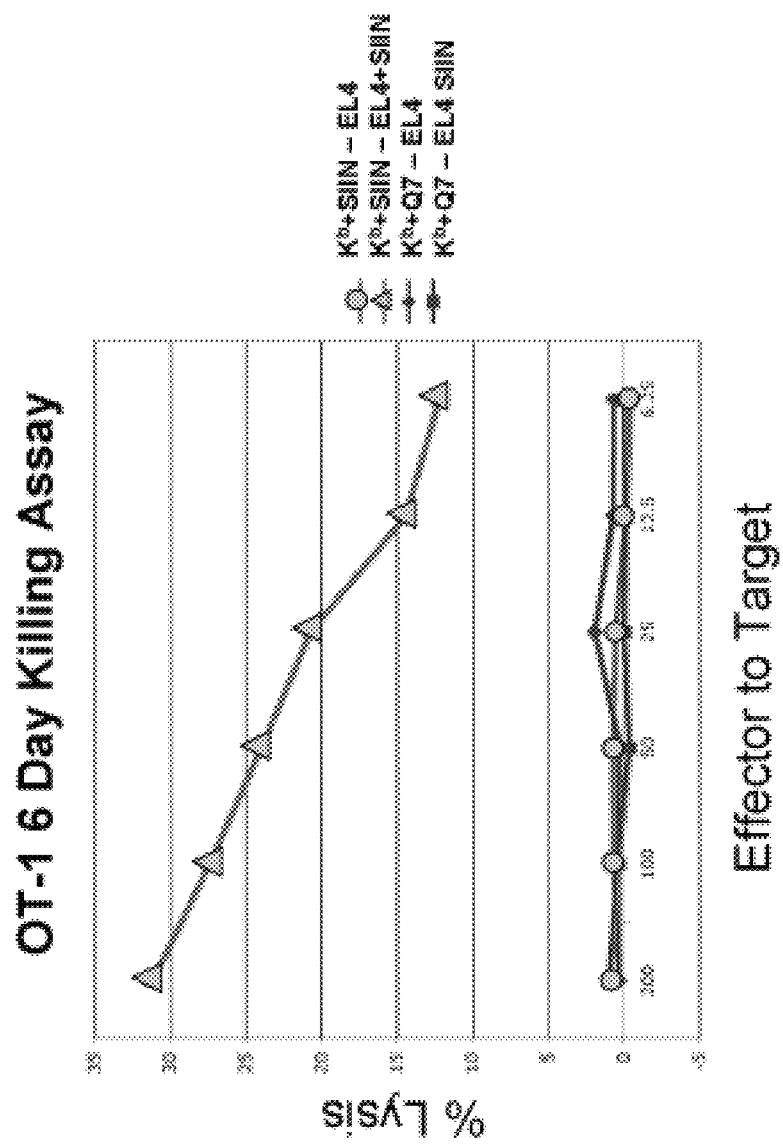
Figure 3:
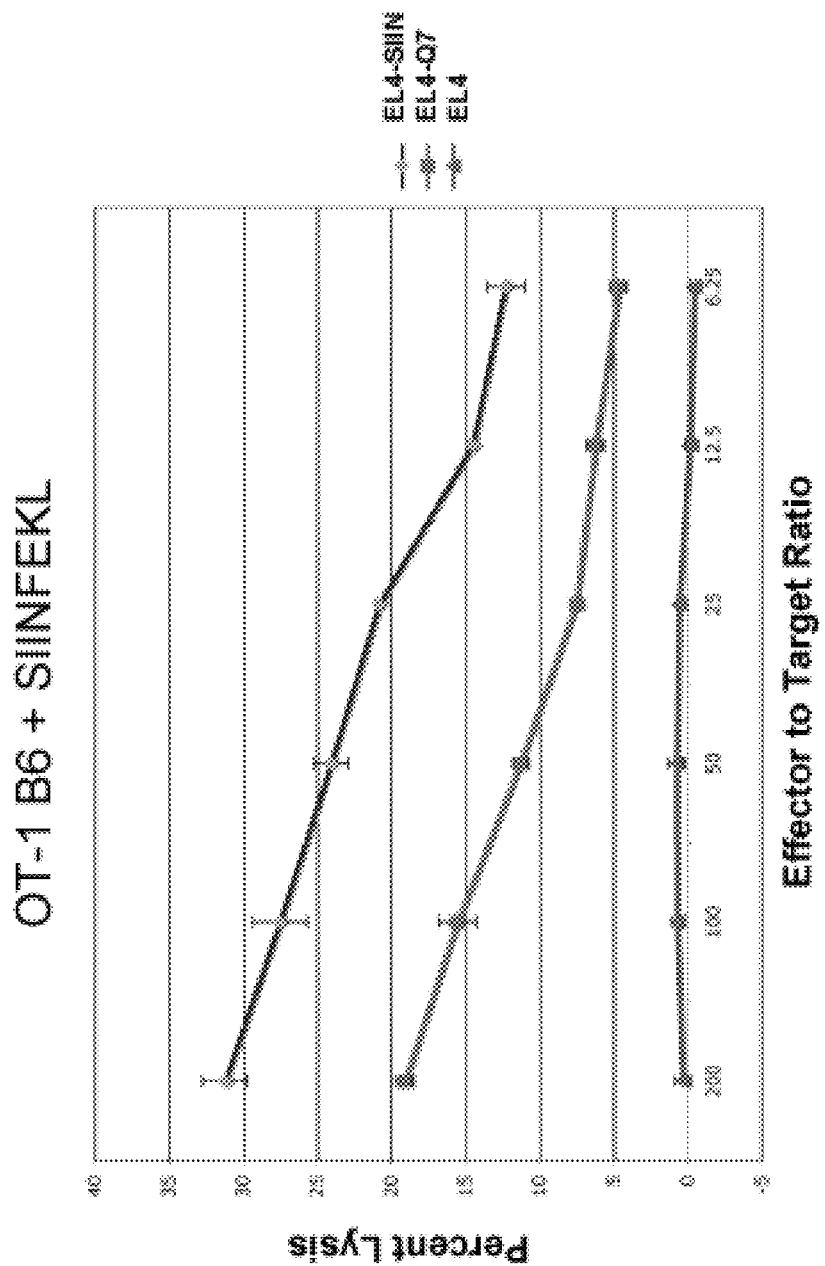

A variant of the SIINFEKL (SEQ ID NO:1) peptide containing a glutamine substitution at position 7 [SIINFEQL (SEQ ID NO:2), also referred to herein as "Q7"] bound H-2K$^b$ comparably to SIINFEKL (SEQ ID NO: 1) (Daniels et al. (2006) *Nature* 444:724-729), but the H-2K$^b$-Q7 ligand did not bind the OT-1 T cell receptor with sufficient affinity to prime naïve OT-1 T cells (FIG. 2). Once primed, however, OT-1 T cells recognized cells expressing H-2K$^b$-Q7 ligand sufficiently to be reactivated, and lysis occurred (FIG. 3). Similarly, binding of Ab 25-D1.16 to H-2K$^b$ was substantially reduced when K$^b$ was complexed with Q7, relative to K$^b$ complexed with SIINFEKL (SEQ ID NO:1) (Table 1). Reduction in binding also was seen, albeit to a lesser degree, with other peptide variants of SIINFEKL (SEQ ID NO:1) (see K$^b$ WT row in Table 1).

To assess whether mutations of the MHC protein could enhance receptor affinity for a MHC-peptide ligand, a model was developed for a peptide specific receptor-ligand interaction using the antibody 25-D1.16 as the receptor, H-2K$^b$ as the MHC peptide presenting molecule, and the SIINFEKL (SEQ ID NO:1) variants E1 (SEQ ID NO:3), G4 (SEQ ID NO: 4), Q7 (SEQ ID NO:2), and Q4H7 (SEQ ID NO:5) as the weak receptor binding peptide ligands. This model emulates the low binding affinity that a T cell receptor retained in the immune repertoire would have for a self peptide. A library of cells expressing H-2$K^b$ and closely related variants containing defined amino acid substitutions in the MHC peptide presenting protein was screened. Antibody 25-D1.16 bound substantially better to three of the MHC variants in complex with variant peptides than it bound to $K^b$ WT in complex with the same peptides (Table 1, and FIG. 2). Most dramatic was the variant $K^{bm3}$ containing an Asp to Ser amino acid substitution at position 77 and a Lys to Ala substitution at position 89 of the mature MHC glycoprotein (FIG. 1C). The $K^{bm3}$ MHC variant bound to other peptides was not bound appreciably by Ab 25-D1.16, demonstrating the peptide-specific nature of interaction between altered MHC-peptide ligand and receptor. Similarly, the increases in binding seen with 65 Gln to Arg with the G4 peptide variant and 24 Glu to Ser with the Q4H7 peptide variant also were peptide-specific. These experiments demonstrated that it is possible to alter the MHC peptide presenting molecule in such a way as to increase the affinity between the MHC ligand and a receptor for that ligand, while retaining the peptide specificity of the interaction.

Biological Significance: The example using 25-D1.16 antibody as a model for the interaction between T cell receptors and altered MHC-peptide ligands illustrated the principle that a mutation in the MHC molecule can enhance binding of the MHC-peptide ligand to peptide-specific receptors. Fundamental to this scheme for activating an immune response against self peptide is the oligoclonality of the repertoire of T cells expressing receptors with subthreshold affinity for the peptide self antigen of interest. Only a subset of such T cells needs to be activated by this scheme to induce a productive immune response. Presumably the activated cells will undergo clonal expansion to generate a population of primed T cells capable of lysing cells expressing the self-peptide. T cells not activated or energized by interaction with the MHC variant ligands would become irrelevant to the ensuing response.

To test whether the $K^{bm3}$ mutation had any measurable biological activity on the OT-1 T cell receptor, a sensitive model for detecting autoimmune T cell activity in vivo was employed. Type I diabetes (TID) is a chronic autoimmune disease in which pancreatic B-cells (which secrete insulin) are selectively destroyed. It is thought to be a T helper 1 mediated disease that involves $CD8^+$ T cells and innate immune cells. Individuals with TID develop hyperglycemia and can develop diabetes-associated complications in several organ systems due to a lack of insulin (Lehuen et al. (2010) *Nat. Rev. Immunol.* 10:501-513).

A mouse model of TID is the RIP-OVA mouse, which expresses OVA under the control of the rat insulin promoter. These mice were crossed with OT-1 mice, which have class I-restricted OVA-specific $CD8^+$ T cells (Blanas et al., *Science* (1996) 274:1707-1709). The mice spontaneously develop diabetes characterized by increased urine glucose levels and infiltration of islets.

B6-RIP-OVA mice are functionally normal and are not responsive to the SIINFEKL (SEQ ID NO:1) peptide antigen, as this fragment of ovalbumin is a self peptide in this model. When B6-RIP-$OVA^{hi}$ mice received $5\times10^5$ naïve OT-1 spleen cells to fill the hole in the T cell repertoire caused by endogenous expression of soluble chicken ovalbumin in the pancreas, thymus, and kidney (and possibly other unknown tissues), they did not develop autoimmune diabetes unless treated further. Challenge of mice harboring OT-1 cells with a Thyleirs murine encephalomyelitis virus (TMEV) expressing SIINFEKL (SEQ ID NO:1) induced diabetes within ten days. As few as 100 naïve OT-1 cells can transfer the ability to respond to the virus as judged by diabetes onset.

The initial test for enhanced antigen presentation by the Kbm3 mutant MHC peptide presenting molecule was to transfer $5\times10^5$ naïve OT-1 T cells into the B6-RIP-$OVA^{hi}$ hosts and immunize them intravenously with engineered antigen presenting cells expressing wild type $K^b$ or a $K^b$ variant containing the 77 Asp to Ser mutation. The engineered antigen presenting cells were prepared from the TAP deficient RMAS cell (Attay et al., *Nature* (1992) 355:647-649), a B cell line which expresses $K^b$ and the co-stimulatory molecule CD80. CD80, CD86, and Kbm3 were introduced into the RMAS cells by DNA mediated gene transfer. Cell lines expressing CD80 and CD86 with or without Kbm3 were established. $10^6$ Q7 (SEQ ID NO:2) peptide-pulsed, TAP deficient RMAS cells expressing transfected CD80/CD86 with or without H-$2K^{bm3}$ were monitored for 2 weeks; none developed diabetes (Table 2). As a positive control, RMAS cells pulsed with SIINFEKL (SEQ ID NO:1) were included in the experiment. These mice also did not develop diabetes. This result was interpreted to indicate that the engineered antigen presenting cells were not able to prime the T cell response to the extent needed to induce diabetes in this model.

In the context of the model, the Kbm3 mutation may not optimize, from a functional perspective, the affinity of the altered MHC-peptide ligand for the OT-1 T cell receptor. It was hypothesized that while the enhanced affinity of the alter MHC-peptide ligand may not provide a fully activating signal to the OT-1 T cells, it may still provide a signal sufficient to enhance the ability of the OT-1 cells to persist functionally in the toleragenic B6-RIP-OVA$^{hi}$ host environment. To test for the persistence of adoptively transferred OT-1 T cells, the mice in Table 2 were challenged intraperitoneally with a picornavirus expressing SIINFEKL (SEQ ID NO: 1) (on day 15 after the original treatment with RMAS-derived antigen presenting cells). Whereas none of the mice pretreated 15 days prior with RMAS-K$^b$-Q7 pulsed cells developed diabetes, 75% of the mice treated with RMAS-Kbm3-Q7 rapidly developed disease, as did the mice treated with RMAS-K$^b$-SIINFEKL (SEQ ID NO:1). This result was interpreted to mean that the Q7 peptide-pulsed RMAS-Kbm3 antigen presenting cells provided a functional signal to the adoptively transferred OT-1 cells, enhancing their ability to respond to subsequent challenge with a pircornavirus expressing a self antigen. In contrast, RMAS cells expressing the wild type MHC molecule K$^b$ pulsed with the Q7 (SEQ ID NO:2) peptide were not able to respond to self antigen (SIINFEKL; SEQ ID NO:1) presented by this same virus. This result demonstrated that modification of the MHC protein sequence can alter the quality of antigen presentation in vivo, enhancing the potential to develop a T cell response against a self antigen.

TABLE 1

25-D1.16 Binding
MHC heavy chain amino acid replacements influence the ability of
MHC:peptide complexes to function as ligands for the 25-D1.16 antibody

| 1<br>MHC Variant | 2<br>K$^{bm3}$-SIIN/<br>K$^b$-SIIN | 3<br>E1 | 4<br>G4 | 5<br>Q7 | 6<br>Q4H7 |
|---|---|---|---|---|---|
| Kb-WT | 1.00 | .40 | .21 | .003 | .18 |
| 9VH | 0.075 | — | — | — | — |
| 22YF | 1.32 | .01 | .01 | .01 | .04 |
| 24ES | 0.78 | .07 | .04 | .05 | 1.1* |
| 24SA | 0.87 | .003 | .003 | .004 | .004 |
| 62RQ | 0.53 | .01 | .01 | .06 | .07 |
| 63EI | 1.10 | .38 | .12 | .04 | .02 |
| 65QR | 0.74 | .01 | 1.21* | .001 | .001 |
| 66KN | 1.43 | .21 | .11 | .04 | .16 |
| 67AS | 1.12 | .004 | .34 | .01 | .09 |
| 69GD | 0.85 | .02 | .01 | .01 | .02 |
| 70NH | 1.05 | .07 | .01 | .03 | .04 |
| 73SW | 0.00 | — | — | — | — |
| 74FS | 1.05 | .12 | .07 | 0 | 0 |
| 77DS | 0.41 | .04 | .01 | .76* | .02 |
| 77DS, 89KA | 0.85 | .18 | .006 | .75* | .003 |
| 81LA | 0.60 | .01 | .01 | .01 | .01 |
| 82LQ | 0.89 | .40 | .18 | .11 | .16 |
| 95IL | 1.31 | .42 | .18 | .003 | .29 |
| 99SY | 0.77 | .06 | .01 | .004 | .004 |
| 116YH | 0.14 | — | — | — | — |
| 116YS | 1.00 | .004 | .01 | .03 | .04 |
| 116YV | 1.43 | .29 | .11 | .01 | .12 |
| 167WS | 0.65 | .53 | .21 | .001 | .005 |

LTK cells were transfected with K$^b$ wild type (WT) or mutant genes encoding MHCs with the indicated amino acid substitutions (Column 1). The ability of the variant molecules relative to the WT molecule when complexed with SIINFEKL (SEQ ID NO:1) to be bound by antibody 25-D1.16 (Column 2) was determined by pulsing the cultured cells with 10 µg/ml peptide for one hour prior to washing and staining with antibody for analysis by flow cytometry. Median fluorescent intensity (stained-unstained) was used as an estimate of binding. The ability of each variant MHC complexed with the SIINFEKL (SEQ ID NO:1) variants (E replacement at position 1, G replacement at position 4, Q replacement at position 7, and Q at 4 and H at 7 double replacement) to bind antibody 25-D1.16, relative to the ability of the same variant complexed with SIINFEKL (SEQ ID NO:1) to bind 25-D1.16 are shown in Columns 3-6. Comparisons were drawn only for variants that bound SIINFEKL (SEQ ID NO:1) at least 25% as well as WT K$^b$ bound the peptide. Substantially increased binding to 25-D1.16 antibody by a MHC heavy chain variant relative to the WT molecule when complexed to a given peptide is represented in the cells labeled with *.

TABLE 2

The K$^{bm3}$-Q7 ligand provides an activation signal to OT-1 T cells
Diabetes Onset in B6-RIP-OVA mice

| Vaccine<br>Day 1 | Day 14<br>Diabetes | Day 15 Challenge with<br>TMEV-SIINFEKL<br>(SEQ ID NO: 1) | Day 21<br>Diabetes |
|---|---|---|---|
| RMAS(K$^b$)-SIINFEKL<br>(SEQ ID NO: 1) | 0/2 | Yes | 2/2 |
| RMAS(K$^b$)-Q7 | 0/4 | Yes | 0/4 |
| RMAS-K$^{bm3}$-Q7 | 0/4 | Yes | 3/4 |

B6-RIP-OVA mice received 5×10$^5$ naïve OT-1 spleen cells followed by 10$^6$ of the indicated RMAS cells pulsed with 10 µg/ml of SIINFEKL (SEQ ID NO:1) or Q7 (SEQ ID NO: 2) peptide intravenously. Blood sugar readings were taken daily for 30 days. Animals were judged to have developed diabetes when two successive blood sugar readings exceeded 300 µg/ml on two successive days. On day 15 all mice were challenged intraperitoneally with TMEV expressing the SIINFEKL peptide in its amino terminal leader sequence.

Figure 4:
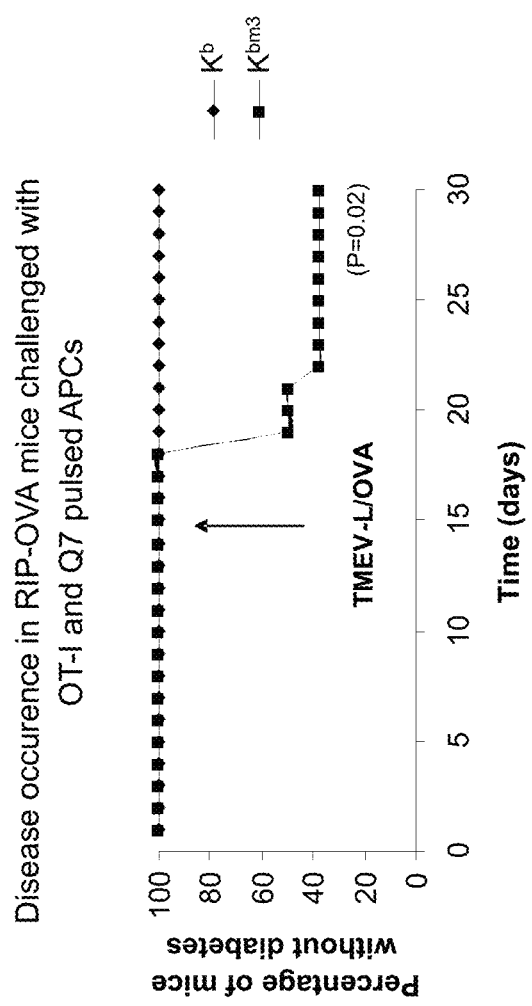

In further experiments, B6-RIP OVA mice received 5×10$^5$ OT-1 T cells and were immunized with RMAS (K$^b$) or RMAS-Kbm3 cells, each pulsed with SIINEFQL (SEQ ID NO: 2; Q7) peptide as antigen, on day 1. On day 15, all mice received 7×10$^4$ TMEV-L/OVA virus challenge ip. Animals were monitored for diabetes (>300 mg/dL blood glucose) for 30 days from the time of OT-1 T cell adoptive transfer. None of the mice pretreated 15 days prior with RMAS-K$^b$-Q7 pulsed cells developed diabetes, but about 65% of the mice treated with RMAS-K$^{bm3}$-Q7 developed disease (FIG. 4).

In summary, the experiments described above suggested the following:

That TMEV-L/OVA specifically drove diabetes in RIP-OVA mice adoptively transferred with OT-1 splenocytes.

That elevated blood glucose levels correlated with pancreatic islet cell invasion.

That varying the amounts of OT-1 splenocytes transferred into RIP-OVA mice along with TMEV-L/OVA correlated with TID development.

Figure 5:
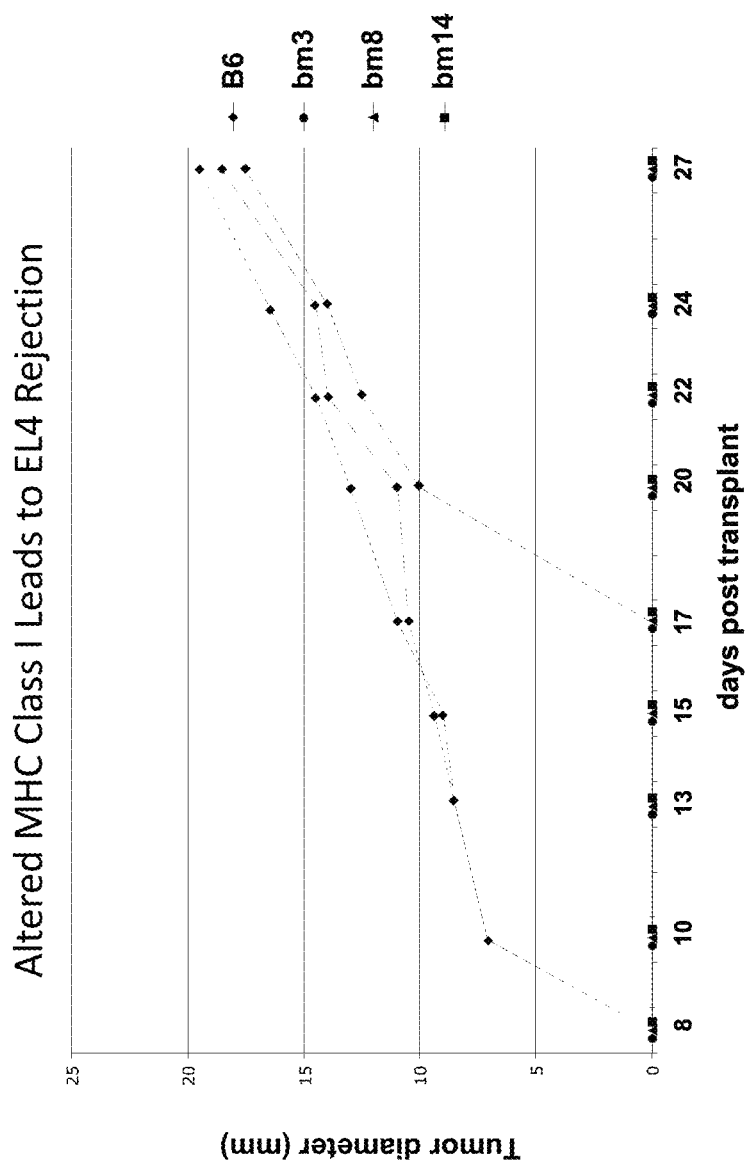

Example 2—Assessing the Ability of Altered MHC Ligands to Induce Protective Immunity Against Native Tumors Experiments showed that EL4 lymphoma tumor grafts mismatched by a single MHC class I mutation that altered peptide binding relative to the host MHC were rejected by the host (FIG. 5). In these experiments, 5×10$^5$ lymphoma cells were introduced subcutaneously into mice genetically matched with the tumor, with the exception of amino acid substitutions in the peptide binding domain of the H-2 K (bm 3 and 8) or D (bm14) class I antigen presenting molecules. The bm3, bm8, and bm14 spontaneous mutations occurred in genetically defined mouse strains and were described previously (Pullen et al. (1989) *J. Immunol.* 143:1674-1679; Hunt et al. (1990) *J. Immunol.* 145:1456-1462; and Hemmi et al. (1988). *J. Exp. Med.* 168 (6): 2319-2335). While the lymphoma cells grew out in the wild type B6 hosts, the tumor did not grow in the mutant mice. This demonstrated that alterations in the structure of MHC molecules with respect to the host resulted in potent anti-tumor resistance. The present approach seeks to use this host response against the variant tumor cells to incite anti-tumor immunity that will cross react back onto the native tumor.

A subsequent experimental scheme is to introduce engineered $^{alt}$MHC ligands into native tumors, and to use these modified tumors as vaccines against the native tumor. If enhanced TcR-MHC affinity is achieved by mutagenesis of the class I a helices, a strong allo reaction is expected such that the altMHC-tumor will fail to grow in the A2 animal. It has been shown, using the spontaneous variant of the K$^{dm5}$ mutant with threonine substituted for alanine at amino acid 158, that alloreactivity was developed in the context of self peptides presented in common by the parental and mutant MHC molecules (Pullen et al. (1994). *J. Immunol.* 152: 3445-3452). $^{alt}$MHC-EL4 cells were generated by transfecting a pCI-vector (Promega Corp., Madison, WI) encoding the altMHC gene into EL4 cells followed by selection of stable transformants expressing the introduced MHC protein on their cell surface by drug selection with G418 (Gibco/Invitrogen; Carlsbad, CA). To test whether cross reactive T cells specific for tumor associated peptides are stimulated by the tumors expressing altMHC molecules, $^{alt}$MHC-expressing EL4 cells are introduced into B6 mice bearing wild type tumor cells, either by simultaneously challenging with tumors expressing altMHC on one flank and wild type tumor on the opposite flank, or by introducing wild type tumors into the hosts prior to treatment with tumors expressing altMHC. The presence of protective cross reactive immunity is detected by comparing the growth of the wild type tumors in mice receiving tumor vaccines bearing altMHC with the growth of wild type tumors in mice receiving a sham wild type vaccine.

To translate this concept from mice to humans, the MHC class I antigen presenting molecule HLA-A0201 is used for initial studies. A0201 is a common MHC class I allele expressed by more than 40% of Caucasians. A guide for generating $^{alt}$A0201 mutations is provided by the contact regions of the α helices of the mouse K$^b$ MHC peptide presentation domain defined by interactions with the 2C TER (MHC aa 72, 76, and 79 for CDR2β and MHC aa 154, 158, 162, and 166 for CDR2a; FIG. 6 and Garcia et al. (1998), supra), as well as the contacts determined for human HLA-A2 that contact A6 TcR (residues 155, 158, 166; FIG. 6). A range of mutations representing changes in size, polarity, and charge are evaluated for their ability to enhance binding (Table 3), as amino acid changes at any or all of these positions may provide optimal stimulation of host T cells while preserving recognition of tumor associated peptides. Efforts are focused on two of these amino acid positions on the wild type HLA-A0201 molecule: $V^{76}$ and $A^{158}$ (i.e., one residue in position to contact the α chain of the T cell receptor and another residue in position to contact the β chain of the T cell receptor). The $Ala^{158}$ to Thr replacement is equivalent to the dm5 mutant mouse, and $Val^{76}$ is in the same area as the A77S mutation found in bm3. Substitution of Ala often is useful to probe structure, as it is considered to be the least disruptive replacement with respect to secondary structure. In the case of $A^{158}$, Val is the next most similar amino acid, since Gly tends to disrupt secondary structure. Otherwise, amino acids sharing charge, polarity and similar sizes (by length and mass) are selected as the most similar. The last category of substitutions would result in a change in charge.

As shown in FIG. 6, three amino acids from the CDR2 loop of the TcRα interact closely with amino acids on the MHC heavy chain. Many Vα genes in both the mouse and human systems express different amino acids in these three positions, providing a diversity of potential salt bridges, hydrogen bonding, van der Waal forces, and hydrophobic interactions at TcR:MHC interfaces formed with altered A2 molecules. Comparison of atomic contacts of three different mouse TcR(s) specific for the same peptide epitope presented by single MHC molecule has documented this point (Feng et al. (2007) *Nat. Immunol.* 8 (9): 975-983). Substitutions are made at any of the conserved positions on the MHC heavy chain along the contact region with CDR2α ($E^{154}$, $A^{158}$, $G^{162}$, and $E^{166}$) to determine whether the ability of TcR(s) to interact with the altMHC-ligand is altered. Some substitutions are expected to be destabilizing, but other mutations are expected to enhance binding. Variation in the contact positions for CDR2 of TcR Vβ with MHCα1 helix amino acids $Q^{72}$, $V^{76}$, and $R^{79}$ is just as extensive, providing two regions of the MHC:TcR interface to manipulate while leaving peptide binding to the MHC antigen presenting molecule and the TcR unchanged.

To begin these studies, the eight MHC mutants listed in Table 3 for positions 76 and 158 were generated by creating genes encoding the HLA-A0201 protein with single amino acid substitutions at those positions (Val to Ala, Gly, Thr, or Glu at residue 76 and Ala to Val, Gly, Thr, or Glu at residue 158). A mouse MHC expression system is used to build HLA-A2 constructs so that the portions of the encoded class I protein that are needed to interact with species specific accessory molecules (e.g., CD8) and intracellular regions of the molecule will function in appropriately in mouse hosts. As with the mouse MHC, the engineered A2 molecules are tagged with antibody epitopes (which do not influence the structure of the peptide and TcR binding domain) and stably-expressing RMAS and EL4 cells are generated (Kuhns et al. (2000) *Proc. Natl. Acad. Sci. USA,* 97 (2): 756-760; and Pullen et al. (supra)). To test how well the altMHC molecules activate naïve T cells in a normal immune repertoire, enhanced allogeneic T cell activation is evaluated in vivo using B6 transgenic host animals expressing wild type HLA-A0201 (i.e., "humanized" A2 mice). $^{WT}$MHC- or $^{alt}$MHC-expressing EL4 mouse tumor cells are grafted onto the A2 mice in a manner similar to the studies for the $^{alt}K^b$ expressing cells.

TABLE 3

| WT Amino Acid | Ala scan | Most Similar | Smaller | Larger | Different Charge |
|---|---|---|---|---|---|
| $Q^{72}$ | A | N | S | R | E |
| $V^{76}$ | A | A | G | T | E |
| $G^{79}$ | A | A | — | R (as in B27) | E |
| $E^{154}$ | A | D | S | R | R |
| $Q^{155}$ | A | N | S | R | E |
| $A^{158}$ | — | V | G | T | E |

TABLE 3-continued

| WT Amino Acid | Ala scan | Most Similar | Smaller | Larger | Different Charge |
|---|---|---|---|---|---|
| $G^{162}$ | A | A | — | T | E |
| $E^{166}$ | A | D | S | R | R |

Delivery of altMHC molecules using virus vectors: Using the current strategy, the $^{alt}$MHC molecule is introduced directly into the tumor cell line by gene mediated transfer. This requires immune recognition to occur by direct recognition of the tumor cells, and minimizes indirect recognition mediated by professional antigen presenting cells such as dendritic cells or macrophages. A vaccination strategy to be examined involves introduction of the altMHC gene directly into tumor cells using virus-based delivery system. For example, the cDNA encoding the altMHC molecule is introduced into an adenovirus vector, high titer virus prepared, and the virus is used to infect tumor cells in situ. This delivery strategy provides an approach for developing a tumor vaccine in patients where the virus is introduced into cancer cells by injection directly into tumor. Immunity induced by the vaccine provides anti-tumor protection systemically, eliminating tumors throughout the body.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A virus particle comprising a nucleic acid that encodes a variant of a wild-type human HLA-A0201 molecule consisting of a non-conservative amino acid substitution of $G^{162}$ to tryptophan, tyrosine, or phenylalanine.

2. The virus particle of claim 1, wherein said virus particle is an adenovirus particle.

* * * * *